United States Patent [19]

Williams

[11] Patent Number: Plant 5,677

[45] Date of Patent: Mar. 4, 1986

[54] **MINIATURE ROSE PLANT *MINJCO'***

[76] Inventor: Ernest D. Williams, 1510 Lebanon Ave., Dallas, Tex. 75208

[21] Appl. No.: 606,397

[22] Filed: May 2, 1984

[51] Int. Cl.[4] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant characterized by the light pink color and exhibition form of buds and flowers.

1 Drawing Figure

The present invention relates to a new and distinct variety of hardy, dwarf, bush type rose plant of the miniature class; the variety being primarily characterized — as to novelty — by light pink, to coral pink color of buds and flowers which in general color effect are similar to Watercolor (miniature — U.S. Plant Pat. No. 4,031).

The variety is further characterized by:

An abundance of bloom, with flowers borne singly (occasionally several) to the stem.

Moderate fragrance.

A plant which is vigorous, of rounded somewhat spreading shape with glossy, small, dark green foliage with pointed leaflets; the buds and flowers being similar in form and size to Over the Rainbow (miniature — U.S. Plant Pat. No. 3,472).

The plant, which has a normal height of about 12 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Little Darling (U.S. Plant Pat. No. 1,581, expired) as the seed parent and Over the Rainbow — miniature (U.S. Plant Pat. No. 3,472), as the pollen parent.

Subsequent to origination of the variety I successfully asexually reproduced it at my nursery, located as aforesaid by cuttings; the reproduction having run true in all respects.

The color photograph illustrates the variety, including the foliage, buds and flowers.

Referring now specifically to the new and distinct variety of miniature rose plant, the following is a detailed description thereof in outline; all major color plate identification being by reference to The British Colour Council Horticultural Colour Chart, except where common terms of color definition are employed.

Type: Hardy; dwarf; rounded; seedling; greenhouse; outdoors; cut flowers; garden decoration; potted plant.

Class: Miniature, Variety name: Minjco. (Commercial Synonym: Loveglo)

Flowers borne: Singly (occasionally several) on slender, wirey stems.

Quantity of bloom: Abundant both outside and in greenhouse.

Bud:

*Peduncle.*—Medium to long; slender but sturdy; erect; medium to light green; hairs — few or none.

*Before calyx breaks; size.*—Small. Form long; pointed with several foliaceous apendages on surface of bud; with foliaceous parts extending beyond the tip of the bud equal to one-half or more of its length.

*Color.*—Medium green.

*As calyx breaks, color.*—Pink, blending into creamy pink near base. Opening: opens well in all weather.

Bloom:

*Size when fully open.*—Small, averaging about $1\frac{1}{4}''$.

*Petalage.*—Averaging about 40–45 petals, arranged regularly plus sometimes occasional petaloids.

*Form.*—High centered with petals rolled loosely outward, and later at maturity full and somewhat rounded. Open flowers may show stamens.

Petals: Fairly thick; satiny on inside and on outside surface.

*Shape.*—Outside petals, broad lanceolate with acute tip; intermediate — broad lanceolate with short acute tip; inside — lanceolate with acute or rounded tip.

Color: Newly opened flower from a plant grown outdoors;

*Outside petal.*—Outside surface — light pink, near Neyron Rose 623/3 blending into lighter (whiteish) pink near base. Inside surface — similar to Neyron Rose 623/3 and often shaded or veined with deeper pink.

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — Color — Light pink. Three days open — Color similar to newly opened flowers but lighter color. Behavior — Opens well in all weather. Spent petals drop off. Flower longevity (May 1983) — Plant in pot 6–8 days or longer. Cut flowers at living room temperature 4–6 days or longer.

Reproductive organs:

*Stamens.*—Few, arranged regularly about pistils.

*Filaments.*—Varying length, medium to long, yellow.

*Anthers.*—Average number.

*Pollen.*—Some.

*Pistils.*—Average number.

*Ovaries.*—All enclosed in calyx.

*Hips.*—Few to none.

*Sepals.*—Permanent; spear shaped; recurved.

*Seed.*—None.

Foliage:

*Leaves.*—Compound of five (sometimes seven) leaflets — small; leathery; glossy.

*Leaflets.*—Shape: broad lanceolate; nearly oval; apex acute; base rounded or rounded acute. Margin: serrate. Color: deep green; new growth — reddish to green. Rachis: medium strength; upper side may have a few tiny short hairs or prickles. Stipules: medium long; narrow to medium width; short length; narrow points which turn out usually at more than 45 degrees.

Growth:

*Habit.*—Dwarf; bushy; rounded; much branched.

*Growth.*—Free; vigorous; internodes short.

*Canes.*—Medium; slender; sturdy.

*Main stems.*—Color: Medium green.

*Thorns.*—Few; small; slender. Prickles — Few or none; hairs — none.

*Branches.*—Color: light to medium green. Thorns: few; small; slender. Medium to short oval base. Prickles: none. Hairs: usually none.

*Young shoots.*—Color: bronze or reddish. Thorns: few or none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, rounded, much branched habit, substantially as illustrated and described, characterized by buds and flowers which are of light pink (to coral pink) coloring, the buds and flowers resembling Over the Rainbow (miniature — U.S. Plant Pat. No. 3,472) in form and size, produced on a plant of compact growth habit; and further characterized by (1) a plant which is easy to propagate from soft wood cuttings and (2) a plant with deep green, glossy, disease resistant foliage, with an abundance of flowers usually borne singly on slender wirey stems.

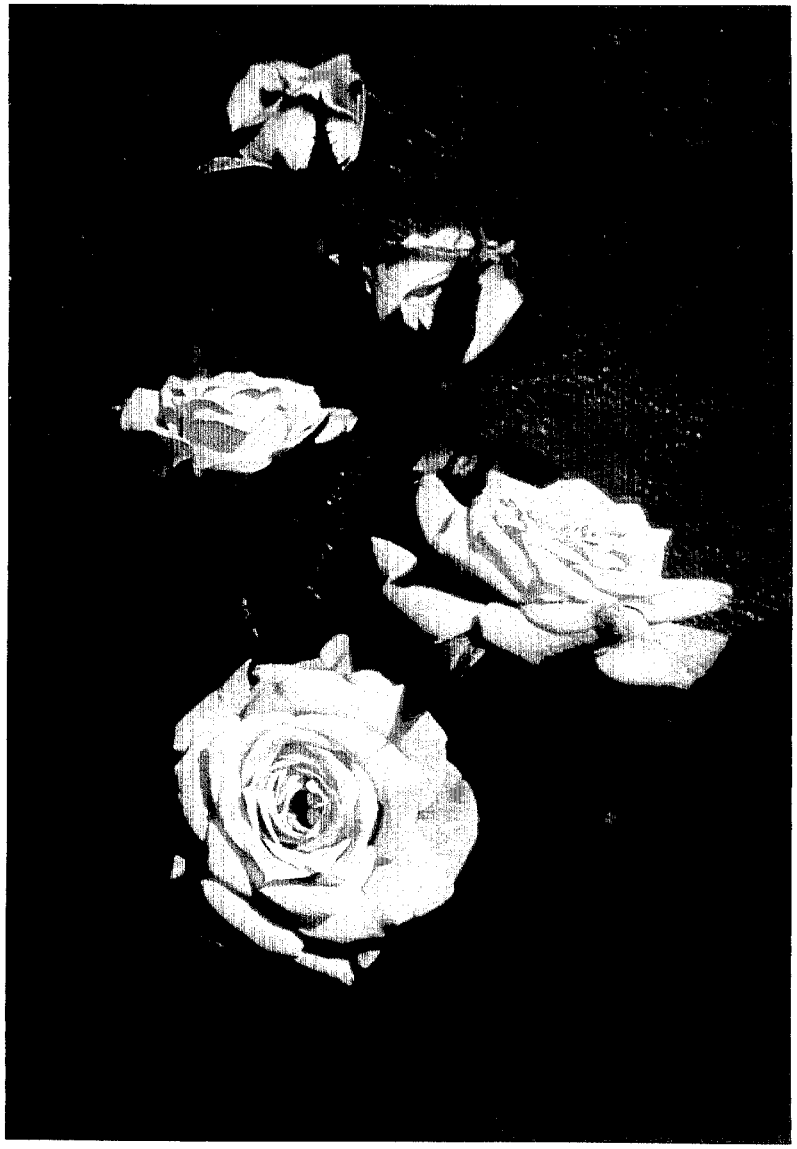

* * * * *